(12) United States Patent
Wickstead et al.

(10) Patent No.: US 6,191,497 B1
(45) Date of Patent: Feb. 20, 2001

(54) SPIROMETER COUNTER CIRCUIT

(75) Inventors: James C. Wickstead, Mendham; Brian Forbes, Lincoln Park; Michael J. Keating, Blairstown, all of NJ (US)

(73) Assignee: DHD Healthcare Corporation, Canastota, NY (US)

( * ) Notice: Under 35 U.S.C. 154(b), the term of this patent shall be extended for 0 days.

(21) Appl. No.: 09/382,441

(22) Filed: Aug. 25, 1999

(51) Int. Cl.⁷ ....................................................... H02J 1/00
(52) U.S. Cl. .............................................. 307/11; 307/125
(58) Field of Search ................................. 307/11, 52, 125; 348/743; 323/282; 713/322, 323; 600/538

(56) References Cited

U.S. PATENT DOCUMENTS

| | | |
|---|---|---|
| 3,432,678 | 3/1969 | Larson . |
| 3,448,361 | 6/1969 | Dinter . |
| 4,495,944 | 1/1985 | Brisson . |
| 4,672,232 | 6/1987 | Schoen . |
| 5,165,417 | 11/1992 | Murphy, Jr. . |
| 5,523,802 * | 6/1996 | Sugihara et al. ...................... 348/743 |
| 5,560,353 | 10/1996 | Willemot . |
| 5,708,357 * | 1/1998 | Chen ................................... 323/282 |
| 5,717,258 * | 2/1998 | Park ................................... 307/125 |

* cited by examiner

Primary Examiner—Stephen W. Jackson
Assistant Examiner—Sharon Polk
(74) Attorney, Agent, or Firm—August E. Roehrig, Jr; Hancock & Estabrook, LLP

(57) ABSTRACT

A single switch is utilized within a common ground line to control the current flow through a plurality of loads, whereby power to all of these loads may be interrupted by opening the system ground return so that power can be supplied to a particular component of the circuit, a microprocessor, to the exclusion of all remaining components by the operation of a single switch.

10 Claims, 3 Drawing Sheets

SPIROMETER COUNTER CIRCUIT

BACKGROUND OF THE INVENTION

This invention relates in general to an electrical circuit which is capable of isolating particular components while supplying power to a particular device and, more particularly, to an electrical circuit whereby supporting devices in the circuit may be shut down, while power continues to be supplied to a circuit controller without maintaining the surrounding support devices thereby reducing current consumption to near zero.

In the design of electrical circuits, it is customary that the positive supply is opened when it is desired to interrupt or terminate power to the circuit or components thereof. However, when it is desired to supply power to a particular component of a circuit, the particular circuit component can be maintained in an operable condition without maintaining surrounding support devices by shutting down the return mode, not the supply mode of the system, by opening the system ground return rather than interrupting the positive supply. In this manner, the current consumption can be limited to that required for maintaining the particular circuit component active, and has many practical applications wherein it is desired to conserve a power supply such as a battery.

Interrupting the power supply to a circuit by opening the system ground return rather than the positive supply is known to those skilled in the art, and has been used in circuits for such things as power line load control, U.S. Pat. No. 3,448,361, and in a timing controller, in U.S. Pat. No. 4,672,232. In U.S. Pat. No. 3,448,361, "SELECTIVE-FREQUENCY POWER LINE LOAD CONTROL", a semiconductor controlled rectifier (SCR) is coupled between an individual load coupled to a power line, and ground. In operation an individual load is coupled in series with the SCR across the power lines, and when the control electrode of the SCR is triggered "on" by a control voltage, current flows through the load. Current flow is interrupted when the control electrode is not triggered, thereby interrupting power to the load on the system ground return. In U.S. Pat. No. 4,672,232, "MICROPROCESSOR OPERATED TIMING CONTROLLER", an electronic switching device is coupled between an individual load, an appliance receiving receptacle, and ground. In operation the electronic switch is controlled by a microprocessor, which closes the switch to complete a circuit for energizing the receptacle. In the absence of a control signal from the microprocessor, the electronic switch opens the return path to ground, and the appliance plugged into the receptacle is turned off.

In the instant circuit, a single switch is utilized within a common ground line to control the current flow through a plurality of loads, whereby power to all of these loads may be interrupted by opening the system ground return so that power can be supplied to a particular component of the circuit, a microprocessor, to the exclusion of all remaining components by the operation of a single switch.

SUMMARY OF THE INVENTION

It is an object of this invention to more efficiently utilize power supplied to an electrical circuit, including a plurality of circuit components and associated support devices.

Another object of this invention is to maintain a supply of power to a particular device in an electrical circuit at all times while selectively interrupting the power supplied to the remaining circuit devices receiving power from the same power supply.

A further object of this invention is to interrupt the power supplied to a plurality of loads coupled to a common power supply through the use of a single switch while maintaining power to a particular circuit component from the same power supply.

Still another object of this invention is to reduce the current consumption of an electrical circuit by opening the system ground to terminate the power supplied to a plurality of loads coupled to the circuit while maintaining the power supply to a particular component of the circuit.

These and other objects are attained in accordance with the present invention wherein there is provided an electrical circuit including a microprocessor or controller to which power is supplied at all times and a plurality of supporting devices to which power to the support devices maybe interrupted by operation of a single switch situated within a common ground line for the plurality of support devices, controlled by operation of the microprocessor controller.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

This and additional embodiments of the invention may now be better understood by referring to the following detailed description of the invention wherein the illustrated embodiment is described.

DETAILED DESCRIPTION OF THE INVENTION

Throughout this description, a preferred embodiment and the examples shown should be considered as exemplars, rather than limitations on the apparatus and methods of the present invention.

Figure 1:
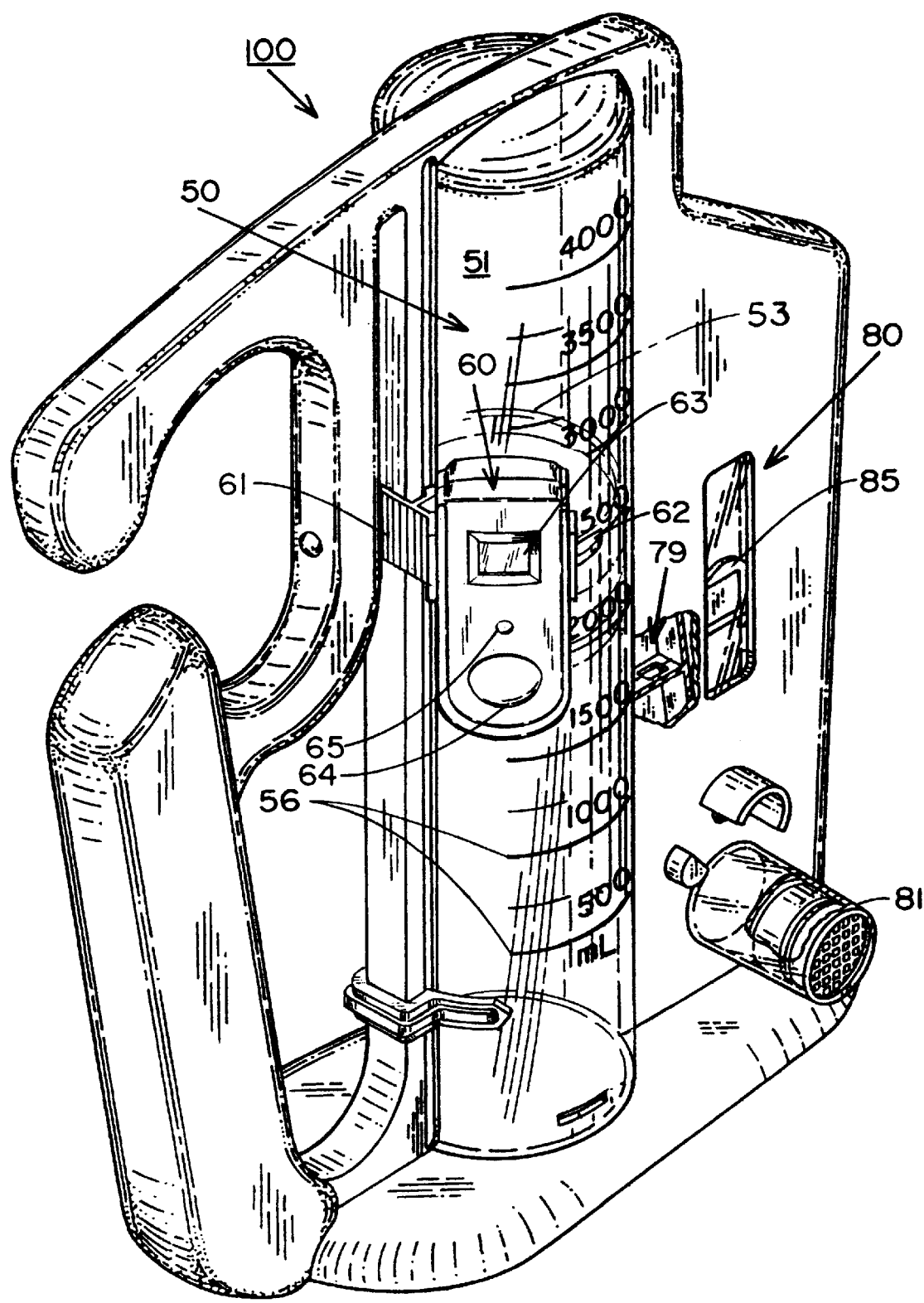
FIG. 1 is a frontal perspective view of an incentive spirometer with a detachable goal-recording counter supported thereon in a position to record the occurrence of a completed predetermined event and incorporating the invention of this application.
Figure 2:
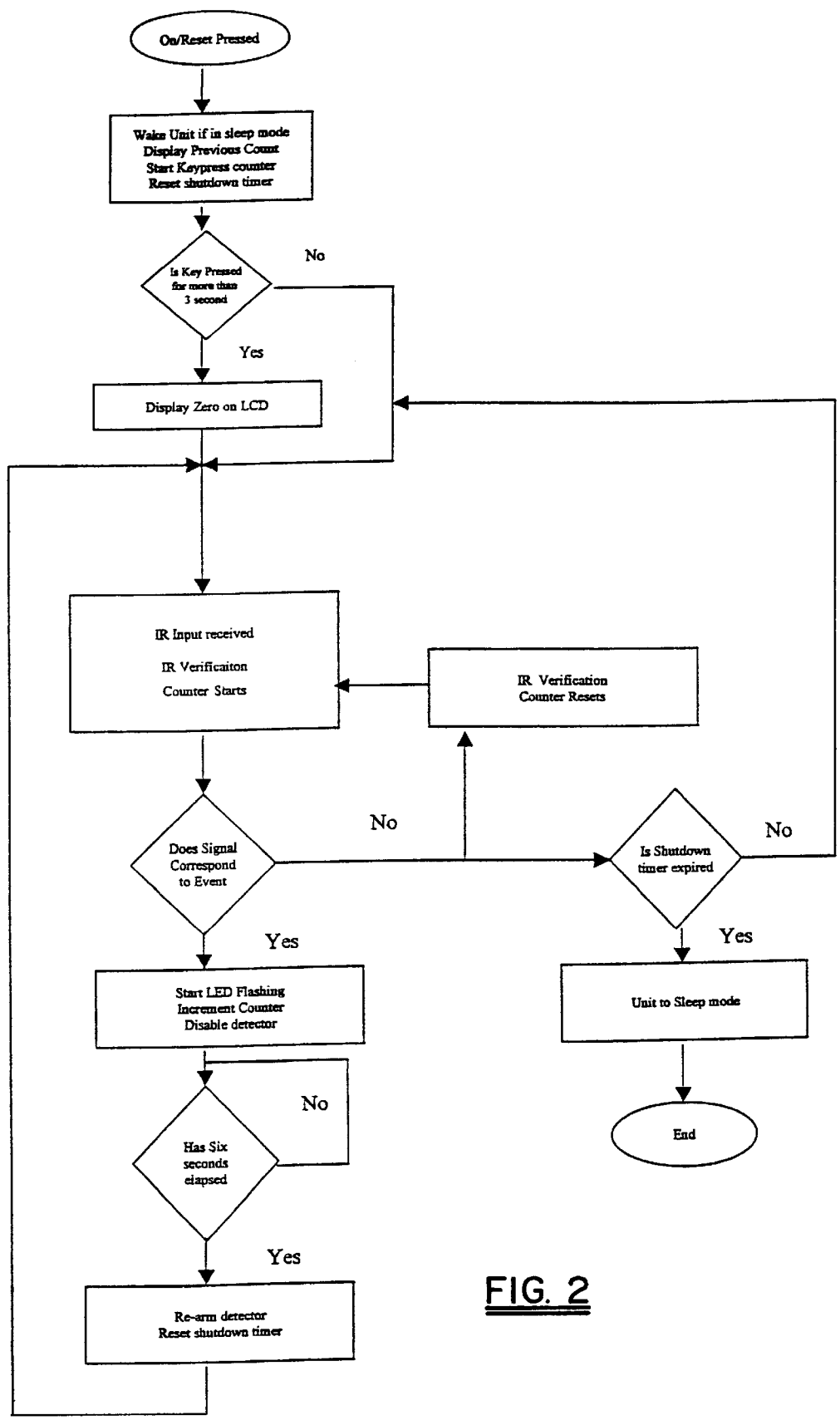
FIG. 2 is a logic block diagram or flow chart to better illustrate the manner in which the electrical circuit of the goal-recording counter records the occurrence of a properly executed event and displays to a user when such a properly executed event has been performed.
Figure 3:
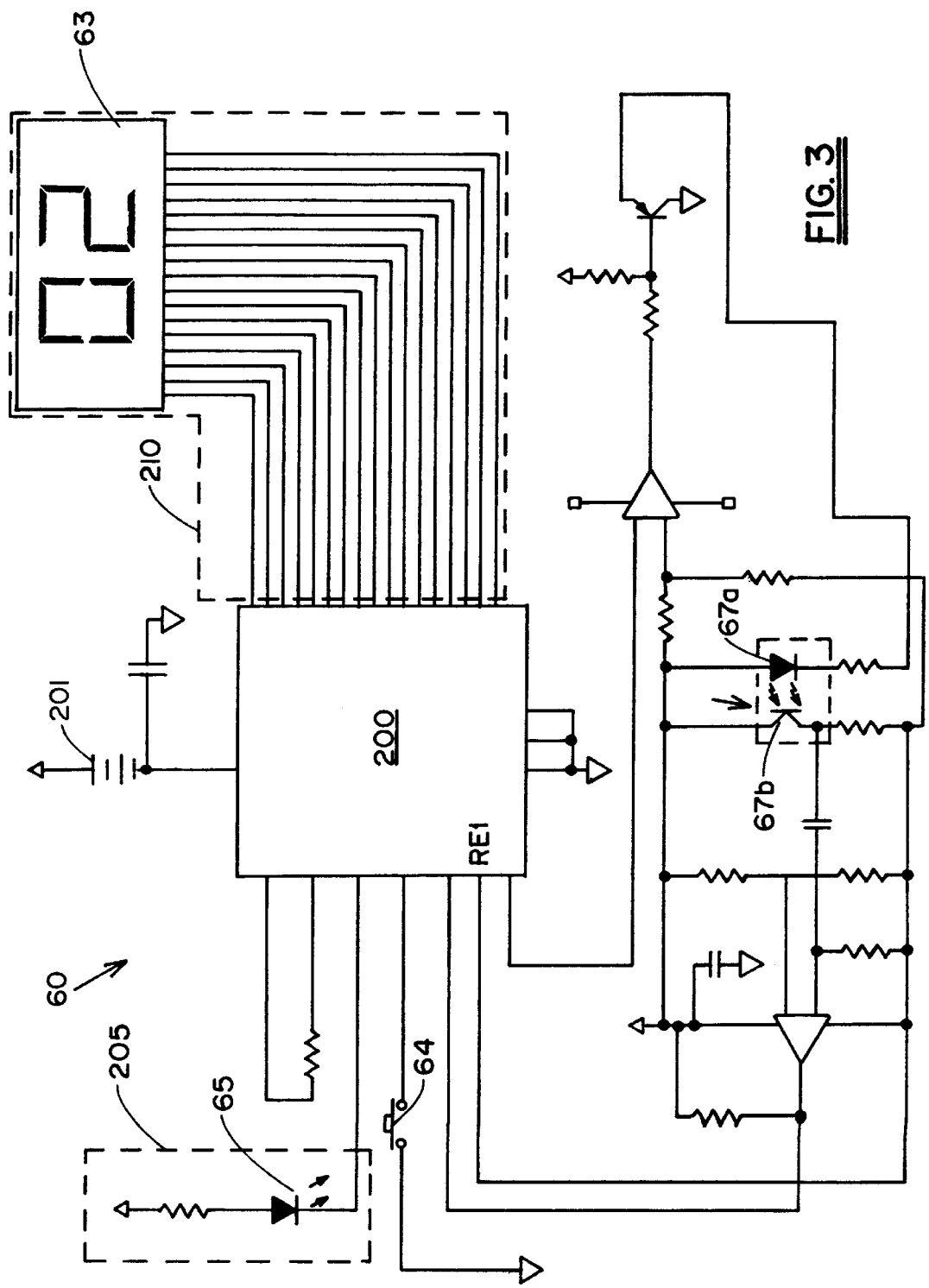
FIG. 3 is an electrical schematic of the present invention which illustrates the manner in which a common power source provides power to a microprocessor or controller and to a plurality of loads corresponding to support devices and in which the power supplied to the plurality of support devices may be terminated by opening the common ground line for such support devices through the operation of a single electronic switch situated within the microprocessor.

Referring now to FIGS. 1–3, there is shown an incentive spirometer 100 having a volume chamber portion 50, carrying a movable piston 53 within, and a goal-recording counter (GRC) which embodies the present invention. The volume chamber portion 50 provides a predetermined volume against which a patient's respiratory system is exercised for a determinable volumetric capacity to obtain the benefits of respiratory therapy. The GRC 60 is readily attachable and removable from the spirometer 100, and informs a patient as to the number of times a predetermined breathing exercise, a proper event, has been properly performed. A monitoring portion 80 provides a visual display to the patient for determining the correct flow rate of inspiratory air to be applied by the patient's respiratory system during therapy, and in cooperation with the GRC 60 and volume chamber portion 50, permits the patient to determine the quality of inspiratory air which has been drawn into the patient's lungs at the desired correct flow rate. For further details of the incentive spirometer illustrated, reference is had to co-pending application, Ser. No. 09/009,338, filed Jan. 20, 1998 in the name of Douglas M. Crumb, et al, the disclosure of which is incorporated herein by reference.

The volume chamber portion 50 of the incentive spirometer 100 includes a chamber 51 of a predetermined volume in which the piston 53 is carried. An air channel (not shown) forms a fluid connection between an inspiratory air inlet port 81 through which a patient draws inspiratory air, and the top (not shown) of the volume chamber 51. In this manner, when a patient draws inspiratory air, the piston 53 is drawn upwardly. If a patient is drawing inspiratory air at the desired target flow rate as shown by an indicator 85, the volume of air drawn into the patient's respiratory system can be determined by observing the calibrations 56 marked on the chamber 51.

The GRC is attached to a portion of the chamber 51 by means of a removable mounting bracket 61, which releasably connects the GRC 60 to the chamber 51. An indicator 62, formed on a portion of the mounting bracket 61, is positioned at a preselected one of the volume calibration marks 56 which corresponds to the volume of air which is desired to be drawn into the patient's lungs when using the device. A count of the number of occasions upon which a patient draws the desired volume of air into the lungs, a proper event, is visually displayed on a display panel 63 of the GRC. When the patient inhales a sufficient volume of air to actuate the GRC, a lamp or light emitting diode (LED) 65 is flashed for a predetermined period of time "coaching" the patient to hold their breath during the time that the LED is illuminated. The manner in which the GRC 60 is actuated to record the number of occurrences in which a patient has successfully performed the proper event, the desired breathing exercise, and the manner in which the LED 65 is flashed to coach the patient in the proper performance of the exercise, is described in detail hereinafter with reference to FIGS. 2 and 3, and in co-pending application Improved Incentive Spirometer, Ser. No. 09/382,608, filed in the names of Lawrence A. Weinstein, et al, which is incorporated herein by reference.

The GRC 60 includes an infra-red emitter/detector 67, comprising an IR emitter 67a and an IR detector 67b, such as a Sharp Model No. GP2S40, which is carried at the back side of the GRC 60 to determine the presence of the piston 53 being raised to the position of the indicator 62 in the volume chamber 51. The IR emitter/detector 67 is coupled into the electrical circuit illustrated in FIG. 3 so that the GRC will record only the movement of the piston 53 within the volume chamber 51 to the proper position as set at indicator 62, without being falsely triggered by other occurrences such as electrical noise or spurious IR signals. To this end, when a patient withdraws inspiratory air from the volume chamber 51, the piston 53 carried there within will rise. When the patient has withdrawn a sufficient amount of inspiratory air to raise the piston 53 to the desired level, marked by the indicator 62, the piston 53 will reflect the IR signal emitted from the emitter portion 67a into the detector portion 67b of the IR emitter/detector 67. Upon verification of the presence of the piston 53, the electrical circuit illustrated in FIGS. 2 and 3 will cause a display 63 to be stepped incrementally to show that the desired goal has been obtained by the patient. At the same time, the coaching lamp or LED 65 will flash intermittently for a predetermined time period, preferably six seconds, to "coach" the patient to hold their breath until the light is extinguished. In this manner, the patient is informed that the desired goal has been obtained and maintained for the correct period of time.

Referring now to the logic block diagram or flow chart of FIG. 2, the operation of the GRC 60 will be described in more detail. A preferred embodiment of the electrical circuit of this invention which is incorporated into the GRC 60 is illustrated in FIG. 3. Initially, a power source such as 3-volt coin type battery 201, commonly available as a CR2032, is connected to a high-performance, four-bit microprocessor or micro controller 200, such as Model W741C250, available from Windbon Electronics Corporation America, 2727 North First Street, San Jose, Calif. 95134. To operate the GRC in the manner desired, and as illustrated in the preferred embodiment of FIG. 3, power is supplied to the microprocessor 200 at all times. However, during some operation of the GRC 60, the "sleep" mode, it is desirable that power be supplied only to the microprocessor 200, and not to the supporting devices such as a liquid crystal display (LCD) array 210 through which a number appears on the display panel 63 of the GRC, the light emitting diode (LED) indicator circuit 205 which includes the "coaching" lamp or LED 65, and the infra-red detector circuit 67, supporting devices used in the operation of the GRC. By shutting down all of the supporting devices and maintaining power to only the microprocessor 200 during a particular operational mode, the "sleep" mode, the battery 201 is conserved by reducing the current consumption to near zero.

When power is supplied to the GRC 60 by depressing an on/reset button 64, the GRC will have been in a "sleep" mode, wherein power is being supplied to the microprocessor 200 only, and not to the surrounding support devices. In the "sleep" mode, the GRC retains the count of the previously completed exercises, or proper events. Depression of the on/reset button 64 will either "awaken" the GRC from the "sleep" mode to retain the count of the previously completed exercises, or will reset the GRC to display a "0" in the display window 63 to indicate that the GRC is in condition to record a new cycle of operation beginning with "0" and sequentially recording the number of successfully completed exercises from that point.

If the on/reset button 64 is depressed for more than three seconds, the GRC 60 will awaken and the input to the LCD array 210 will display a "0" to indicate that the GRC is in condition to record a new cycle of operation beginning with the numeral "0" appearing in the window 63. If the on/reset button 64 is depressed for less than three seconds, the GRC 60 will awaken and the LCD array is energized to display in the display window 63 the retained count of how many times a patient has successfully completed an exercise since the last resetting of the GRC to "0". Depression of the on/reset button 64 actuates a key press counter or reset shut down timer circuit within the microcontroller 200 to energize a timing circuit so that after a period of time the GRC will again be placed in a "sleep" mode, in the event that the piston 53 is not elevated by a patient into the predetermined position within the time period set by this shut down counter/timer. If the shut down timer has completed its count down without receiving a proper signal corresponding to the occurrence of a proper event, the elevation of the piston 53 by a patient into the predetermined position, the shut down timer will shut off the power to the surrounding support devices by opening a common path to ground for all these devices, thereby power will be supplied only to the microcontroller 200 placing the GRC again in the "sleep" mode.

When the on/reset button 64 has been depressed, the GRC is placed in condition to determine if a proper event signal has been received. When a proper event signal is received by the detector 67b, the LED indicator circuit 205 will be energized flashing the "coaching" LED 65 and activating an increment counter 63 so that the patient will hold the inhalation for a predetermined time period, preferably six seconds, during which time the LED 65 will remain flashing. At this time, the infra-red detector 67b will be disabled, and an internal shut down timer energized. If the shut down timer expires before a proper event signal has been received to reset the shut down timer, the microcontroller 200 will place the GRC in the "sleep" mode, thereby terminating power to all of the support devices such as the LCD array 210, the LED "coaching" circuit 205 and the infra-red detector circuit 67 by opening the system ground RE1 through the microcontroller 200. Power from the battery 201 will be maintained only to the microcontroller 200 without maintaining the surrounding support devices to reduce the current consumption or drain on the battery 201 to nearly zero.

While this invention has been described in the specification and illustrated in the drawings which reference to a preferred embodiment, the structure of which has been disclosed herein, it will be understood by those skilled in the art to which this invention pertains that various changes maybe made, and equivalents maybe substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims.

It is claimed:

1. An electrical circuit for a circuit controller operable in a first mode to power said circuit controller and a plurality of supporting devices, operable in a second mode to conserve power by terminating the current supplied to all supporting devices while maintaining current to the circuit controller, comprising:

a source of electrical power for supplying an operating current to a circuit controller and a plurality of circuit controller and supporting devices;

a circuit controller coupled to said source of electrical power and operable in response thereto in a first mode to complete a circuit to a plurality of circuit controller supporting devices;

a plurality of circuit controller supporting devices coupled to said source of power and said circuit controller;

said plurality of circuit controller supporting devices coupled to a common ground through said circuit controller; and said circuit controller including a switch coupled to said common ground and operable in a second mode for opening said common ground to terminate the current supplied to said plurality of circuit controller supporting devices while maintaining the current supplied to said circuit controller, thereby reducing the current drawn from said power supply when operating in said second mode.

2. An electrical circuit for a goal-recording counter for recording the occurrence of a predetermined event and operable in a first mode by a circuit controller to determine the occurrence of a predetermined event and to display a presentation of the occurrence, and operable in a second mode to conserve power by terminating the current supplied to all devices supporting the circuit controller while maintaining current to the circuit controller, comprising:

a source of electrical power for supplying an operating current to a circuit controller and supporting devices;

a circuit controller coupled to said source of electrical power and operable in response thereto;

a plurality of circuit controller supporting devices coupled to said source of power and said circuit controller operable in a first mode for determining the occurrence of a predetermined event and to display a presentation of said occurrence;

said plurality of circuit controller supporting devices coupled to a common ground through said circuit controller, and said circuit controller including a switch coupled to said common ground and operable in a second mode for opening said common ground to terminate the current supplied to said plurality of circuit controller supporting devices while maintaining the current supplied to said circuit controller thereby reducing the current drawn from said power supply when operating in said second mode.

3. The electrical circuit of claim 2 wherein said circuit controller supporting devices include:

an indicia display for displaying the occurrence of a predetermined event;

a signal emitter for emitting a signal at a predetermined rate to signal the occurrence of said predetermined event;

a signal receiver for receiving said signal emitted from said signal emitter to determine the occurrence of said predetermined event; and means for comparing said signal received by said signal receiver with said signal emitted from said signal emitter to verify the occurrence of said predetermined event.

4. The electrical circuit of claim 3 wherein said circuit controller supporting devices further include a timed display signal generator for displaying a signal for a predetermined time period upon the verification of the occurrence of said predetermined event.

5. The electrical circuit of claim 3 further including a reset for said circuit controller to control the operation thereof to mutually exclusively display the number of occurrences of said predetermined event or to reset said indicia display to "0" for beginning a new cycle of operation.

6. The electrical circuit of claim 2 wherein said circuit controller further includes a timer for placing said circuit controller in said second mode of operation opening said switch to said common ground and terminating the current supplied to said circuit controller supporting devices if the verification of the occurrence of said predetermined event does not occur within a set period of time.

7. The electrical circuit of claim 2 wherein upon the occurrence of said second mode of operation said circuit controller retains the count of the number of occurrence of said predetermined event.

8. The electrical circuit of claim 5 wherein said reset is operable in a first sequence of operation to retain the count of the number of occurrences of said predetermined event, and in a second sequence to reset indicia display to "0".

9. The electrical circuit of claim 1 wherein said source of electrical power is a battery.

10. The electrical circuit of claim 2 wherein said source of electrical power is a battery.

* * * * *